United States Patent
Laakso et al.

(10) Patent No.: US 6,902,575 B2
(45) Date of Patent: Jun. 7, 2005

(54) STENT DELIVERY APPARATUS AND METHOD

(75) Inventors: Kari Aarne Juhani Laakso, Tampere (FI); Juha-Pekka Nuutinen, Tampere (FI); Claude O. Clerc, Flemington, NJ (US)

(73) Assignee: Linvatec Biomaterials, Inc., Largo, FL (US)

( * ) Notice: Subject to any disclaimer, the term of this patent is extended or adjusted under 35 U.S.C. 154(b) by 205 days.

(21) Appl. No.: 10/025,669

(22) Filed: Dec. 18, 2001

(65) Prior Publication Data

US 2003/0114910 A1 Jun. 19, 2003

(51) Int. Cl.⁷ ............................................. A61F 2/06
(52) U.S. Cl. .................................................... 623/1.11
(58) Field of Search ........................... 623/1.11, 1.23; 606/194, 200

(56) References Cited

U.S. PATENT DOCUMENTS

| | | | |
|---|---|---|---|
| 4,655,771 A | 4/1987 | Wallsten | 623/1 |
| 5,026,377 A | 6/1991 | Burton et al. | 606/108 |
| 5,683,451 A | 11/1997 | Lenker et al. | 623/1 |
| 6,306,163 B1 * | 10/2001 | Fitz | 623/1.12 |
| 6,391,050 B1 * | 5/2002 | Broome | 623/1.11 |
| 6,514,280 B1 | 2/2003 | Gilson | 623/1.11 |
| 6,602,280 B2 * | 8/2003 | Chobotov | 623/1.11 |

* cited by examiner

Primary Examiner—(Jackie) Tan-Uyen T. Ho
(74) Attorney, Agent, or Firm—Synnestvedt & Lechner LLP

(57) ABSTRACT

A method and apparatus for inserting a self expanding stent into a delivery device and delivering the stent into a body lumen. The apparatus comprises an outer tube; an inner tube; a capturing element slidably mounted on the inner tube and including a foldable sleeve, a blocking element fixed to the inner tube adapted to block a stent from being inserted into the sleeve proximally of the blocking element and to block the capturing element from becoming situated distally of a predetermined point relative to said inner tube, the capturing element carried on the inner tube so that the distal end of the sleeve can extend beyond the distal end of the outer tube in an unfolded condition and be drawn into the outer tube by the blocking element. A stent having an end inserted into the sleeve is drawn into the outer tube, thereby becoming captured within the outer tube. The stent is deployed by inserting the delivery apparatus into a body lumen to position the distal end of the tube adjacent the stent deployment site and drawing the outer tube proximally relative to the stent, so as to release the stent from its radially constricted condition.

20 Claims, 7 Drawing Sheets

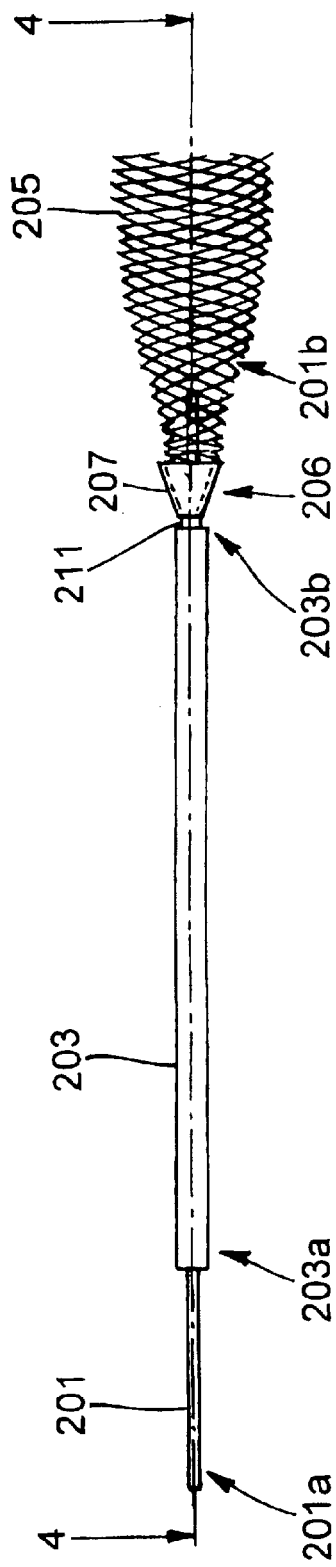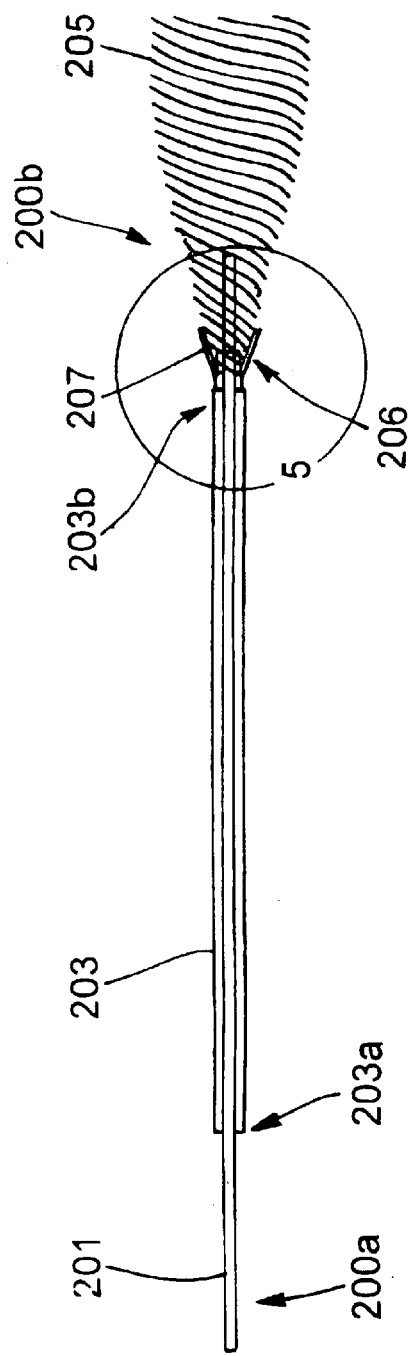
Fig. 3
Fig. 4

STENT DELIVERY APPARATUS AND METHOD

FIELD OF THE INVENTION

The invention pertains to the delivery of self expanding stents, grafts, stent-grafts, covered stents and the like into body lumens. More particularly, the invention pertains to the loading and releasing of self expanding stents and the like from a delivery apparatus.

BACKGROUND OF THE INVENTION

Stents, such as braided or knitted stents for surgical implantation in body lumens (tubular vessels), are known for repairing or strengthening the vessels. A stent essentially is a hollow tube that supplements the body lumen. With respect to the medical condition of stenosis, in which a body lumen tends to collapse or otherwise close, the stent supports the wall of the vessel to prevent it from collapsing or closing. A blood vessel that is narrowed due to the build up of intra-vascular plaque is one example of a stenosis. With respect to the medical condition of aneurism, in which a body lumen is weakened and cannot properly withstand the internal pressure within the vessel and bulges out or ruptures, a graft or stent-graft serves essentially the opposite function in that it substitutes for or supplements a weakened portion of the vessel. Stents are known for insertion in blood vessels, bile ducts, colons, trachea, esophagi, urethra, ureters, nasal passages, ductal systems, etc.

Stents are known that are fabricated from rigid, but flexible materials that, when bent by force, tend to retain the bent shape. Such stents may be inserted into the body lumen in an unstressed, radially minimal shape while mounted over a deflated balloon. When the stent is in situ, the balloon is inflated in order to radially expand the stent, which will then retain the radially expanded shape after the balloon is deflated and removed.

Another type of stent is termed a self-expanding stent. Self-expanding stents can be compressed radially, but will expand to their original shape once the radially constrictive force is removed. Some types of self-expanding stent are formed from materials that are superelastic or have shape memory characteristics. Such stents are commonly made of Nitinol, a biocompatible alloy that, depending on its chemical composition and thermomechanical history, may be either a shape memory material or a superelastic material. The ULTRAFLEX stent manufactured and sold by Boston Scientific Corporation is an example of a knitted Nitinol stent.

Another type of self-expanding stent that reverts to its original shape due to an elastic deformation when radially compressed is exemplified in U.S. Pat. No. 4,655,771, issued to Wallsten and incorporated herein by reference. Walisten discloses a self-expanding, braided surgical dilator stent particularly adapted for coronary dilation, but which can be adapted for use in other body vessels. That patent discloses a stent generally in accordance with the stent 10 shown in FIG. 1A. It comprises a hollow tubular member, the wall of which is formed of a series of individual, flexible, thread elements 12 and 14, each of which extends helically around the central longitudinal axis of the stent. A first subset of the flexible thread elements 12 have the same direction of winding and are displaced relative to each other about the cylindrical surface of the stent. They cross a second plurality of helical thread elements 14 which are also displaced relative to each other about the cylindrical surface of the stent, but having the opposite direction of winding. Accordingly, as shown in FIG. 1A, the threads 12 of the first subset cross the threads 14 of the second subset at crossing points 16.

As the stent is axially stretched, i.e., as the longitudinal ends 18 and 20 are forced away from each other, the diameter reduces, as shown in FIG. 1B. Likewise, if the wall of the stent is radially constricted so as to reduce the stent's diameter, the stent elongates. In other words, radial constriction and axial elongation go hand in hand. When the force is released, the stent tends to spring back to its resting diameter and length.

Bioabsorbable stents also are known in the prior art. Bioabsorbable stents are manufactured from materials that dissolve over an extended period of time when exposed to bodily fluids and are absorbed into the surrounding cells of the body. Various bioabsorbable materials that are suitable for fabricating stents are known in the prior art, including polymers such as poly-L,D-lactic acid, poly-L-lactic acid, poly-D-lactic acid, polyglycolic acid, polylactic acid, polycaprolactone, polydioxanone, poly(lactic acid-ethylene oxide) copolymers, or combinations thereof. Vainionp et al., Prog Polym. Sci., vol. 14, pp. 697–716 (1989); U.S. Pat. No. 4,700,704, U.S. Pat. No. 4,653,497, U.S. Pat. No. 4,649,921, U.S. Pat. No. 4,599,945, U.S. Pat. No. 4,532,928, U.S. Pat. No. 4,605,730, U.S. Pat. No. 4,441,496, and U.S. Pat. No. 4,435,590, all of which are incorporated herein by reference, disclose various compounds from which bioabsorbable stents can be fabricated.

Most, if not all, stents, need to be radially constricted, i.e., reduced in diameter, so that they can be inserted into the body lumen. Then, once they are in situ, the stent can be released and radially expanded.

Various delivery apparatus for delivering a stent into a body lumen in a radially constricted state and then releasing the stent so that it self expands within the body lumen are known. In one popular design illustrated for instance by the device disclosed in U.S. Pat. No. 5,026,377 and shown in FIG. 2, the delivery apparatus comprises an inner tube 5 surrounded by a concentric outer tube 1. The outer tube is shorter than the inner tube so that the inner tube can extend from the outer tube at both ends. A handle 6 typically is provided at the proximal end of the inner tube. Another handle 2 is provided at the proximal end of the outer tube. The inner core is slidable within the outer tube by relative manipulation of the two handles. A stent 11 is loaded within the delivery apparatus captured between the inner and the outer tubes near the distal end of the delivery apparatus.

The inner core may be hollow and adapted to accept a guide-wire 8 which, as is well known in the related arts, can be used to help guide the device to the stent delivery site in the body lumen 4.

During stent delivery, a physician typically will make an incision in the body lumen 4 at a location remote from the stent desired deployment site and then guide the stent delivery device into the body lumen until the distal end of the stent delivery device is at the stent deployment site. The outer tube 1 is then withdrawn proximally while the inner tube 5 is held stationary. Accordingly, the outer tube 1 slides over the stent 11, thus releasing it from radial constriction, whereby the stent radially expands and contacts the wall of the body lumen 4. The stent 11 is held in place by the frictional force between the lumen wall and the stent body resulting from the radial expansion force of the stent. The stent is now fully deployed and the delivery device can be retracted and the procedure concluded.

It is an object of the present invention to provide an improved method and apparatus for delivering a stent into a body lumen.

SUMMARY OF THE INVENTION

The invention is a method and apparatus for delivering a self expanding stent into a body lumen. The apparatus comprises an outer tube having a proximal end and a distal end and sized to hold a self-expanding stent therein in a radially constricted condition; an inner tube within the outer tube and having a proximal end and a distal end; a capturing element slidably mounted on the inner tube and including a foldable sleeve for assisting in radially constricting the stent and inserting it in the delivery apparatus between the two tubes; and a blocking element fixed to the inner tube near the distal end of the inner tube and adapted to pull the capturing element into the outer tube and block a stent inserted into the sleeve from being inserted into the capturing element past a predetermined point. The sleeve has a proximal end and a distal end, with the proximal end being smaller than the outer tube and the distal end being larger than the outer tube. The capturing element is carried on the inner tube such that the distal end of the sleeve can extend beyond the distal end of the outer tube in an unfolded condition and so that the sleeve can be drawn into and become folded within the outer tube when the inner tube is drawn proximally relative to the outer tube. Accordingly, a stent having an end inserted into the distal end of the sleeve can be drawn into the outer tube by drawing the inner tube proximally relative to the outer tube, thereby capturing the stent in a radially constricted condition within the outer tube. The stent is released by axially moving the outer tube proximally with respect to the inner tube. The capturing element is constructed so that it engages and is drawn along with the outer tube when the outer tube moves proximally with respect to the inner tube, thereby freeing the proximal extremity of the stent from the sleeve and allowing unimpeded stent release.

The method is a method of loading a stent into a stent delivery apparatus such as described above comprising the steps of positioning the inner tube such that the distal end of the capturing element extends beyond the distal end of the outer tube; inserting an end of a stent into the sleeve; and drawing the inner tube proximally relative to the outer tube so as to draw the sleeve and the stent into the outer tube, thereby capturing the sleeve and the stent in the outer tube in a radially constricted condition.

BRIEF DESCRIPTION OF THE DRAWINGS

FIG. 3 is a plan view of a stent and stent delivery device in accordance with the present invention.

FIG. 4 is a cross sectional view of the stent and stent delivery device of FIG. 3 taken along line 4—4 in FIG. 3.

DETAILED DESCRIPTION OF THE INVENTION

Figure 1A:
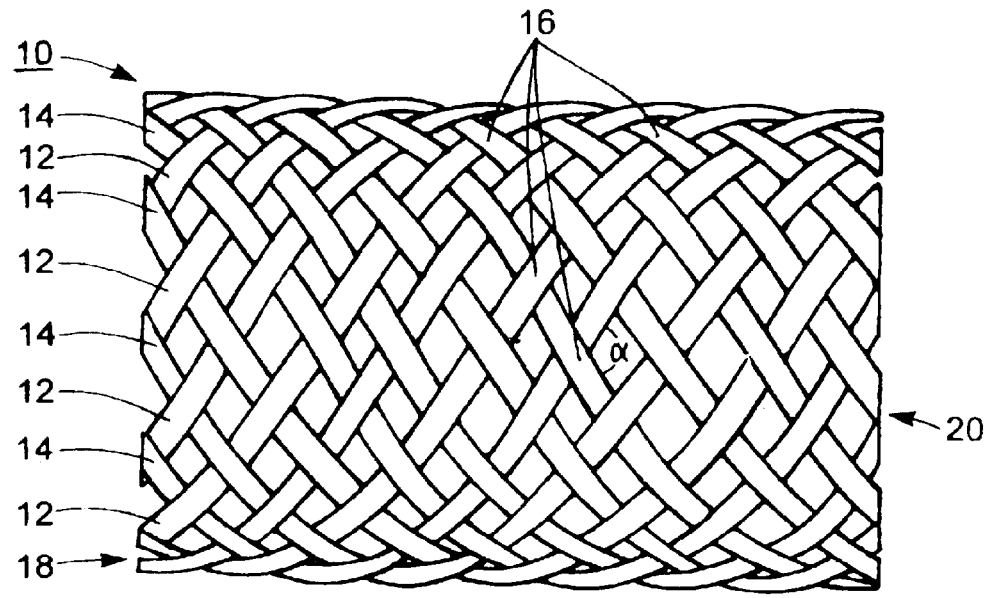
FIG. 1A is a plan view of a braided self expanding stent in accordance with the prior art.
Figure 1B:
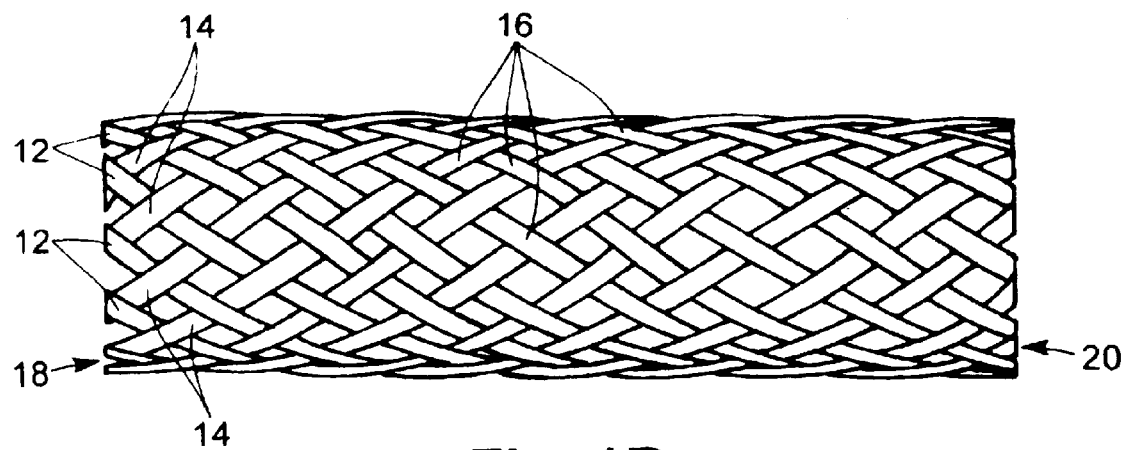
FIG. 1B is a plan view of the stent of FIG. 1A shown in a radially constricted/axially elongated state.
Figure 2:
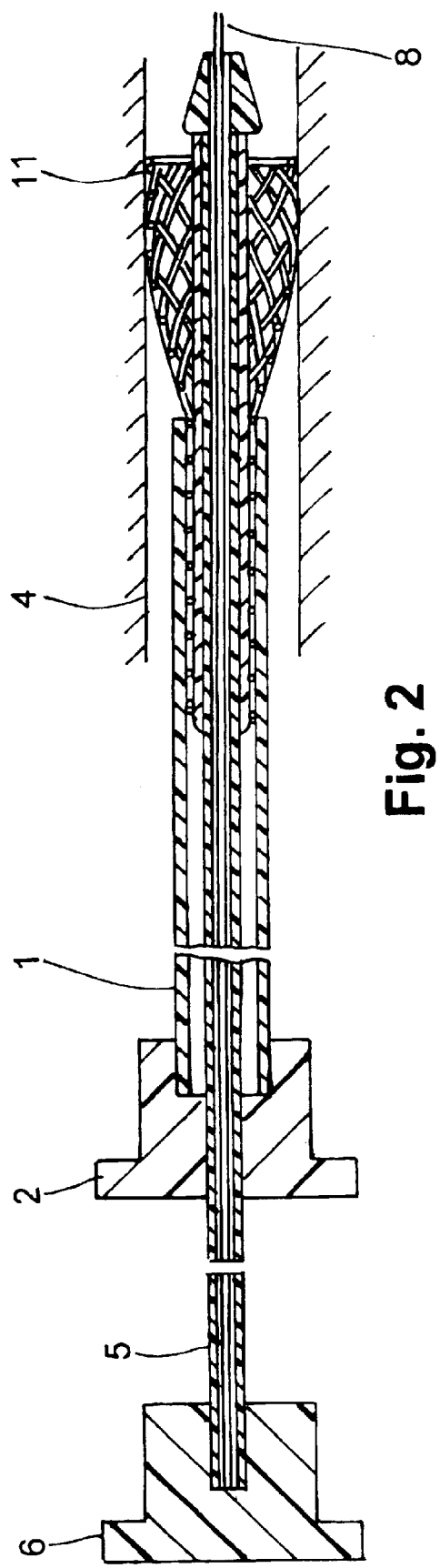
FIG. 2 is a cross sectional view of a conventional stent and stent delivery device.

Bioabsorbable self expanding stents, while having substantial advantages in many respects over metal self expanding stents, also have potential drawbacks. For instance, when bioabsorbable self expanding stents are held in a radially constricted condition for a significant length of time, they tend to take a set and therefore do not fully expand to their original radial diameter when the radial constricting force is released. Even if they are able to expand to their original unrestricted diameter, they may have lower radial expansion force than before they were held in a radially constricted condition for a lengthy period.

It is common for self-expanding stents to be packaged within the stent delivery device at the time of manufacture. Accordingly, no mechanism need be provided for enabling the physician to insert the stent into the stent delivery apparatus since it is received by the physician with the stent already captured in the delivery apparatus. However, the period between the manufacture of a stent/stent delivery device and its actual use in a medical procedure can be substantial. It would not be unusual for this period to be a year or longer. This can be a problem with respect to bioabsorbable self expanding stents for the reasons discussed above.

It will be understood by persons of skill in the art that the cross sectional area of the space between inner tube 201 and outer tube 203 commonly is extremely small and only slightly greater than the thickness of the wall of the stent. Further, depending upon the particular application for the stent, e.g., coronary, the stent and the delivery apparatus can be quite small. Accordingly, it may be extremely difficult, if not impossible, for a physician to properly insert a stent into a stent delivery device by hand. Accordingly, it may be desirable to provide a method and mechanism by which a physician can easily insert a stent into the stent delivery apparatus just prior to the medical procedure so that the stent and stent delivery apparatus can be packaged with the stent outside of the delivery apparatus and in its fully expanded state. The present invention aims to provide such a system.

The invention will first be described in connection with a first particular embodiment illustrated in FIGS. 3, 4, 5, and 6.

FIGS. 3 and 4 are plan and cross sectional views, respectively, of the primary elements of a stent and stent delivery device in accordance with the present invention. It will be understood by those of skill in the art that certain components that are not particularly relevant to the present invention, such as handles, an optional guide wire, and a device tip are not shown for sake of clarity. The delivery device 200 has a proximal end 200a and a distal end 200b. The proximal end is the end that is held in the physician's hand during a medical procedure. The distal end is the end that is inserted into the lumen during a medical procedure. Device 200 comprises an inner tube 201 with a proximal end 201a and a distal end 201b and an outer tube 203 with a proximal end 203a and a distal end 203b. A stent 205 is to be inserted into the delivery device 200 so as to be captured in a radially constricted condition between outer tube 203 and inner tube 201.

Figure 5:
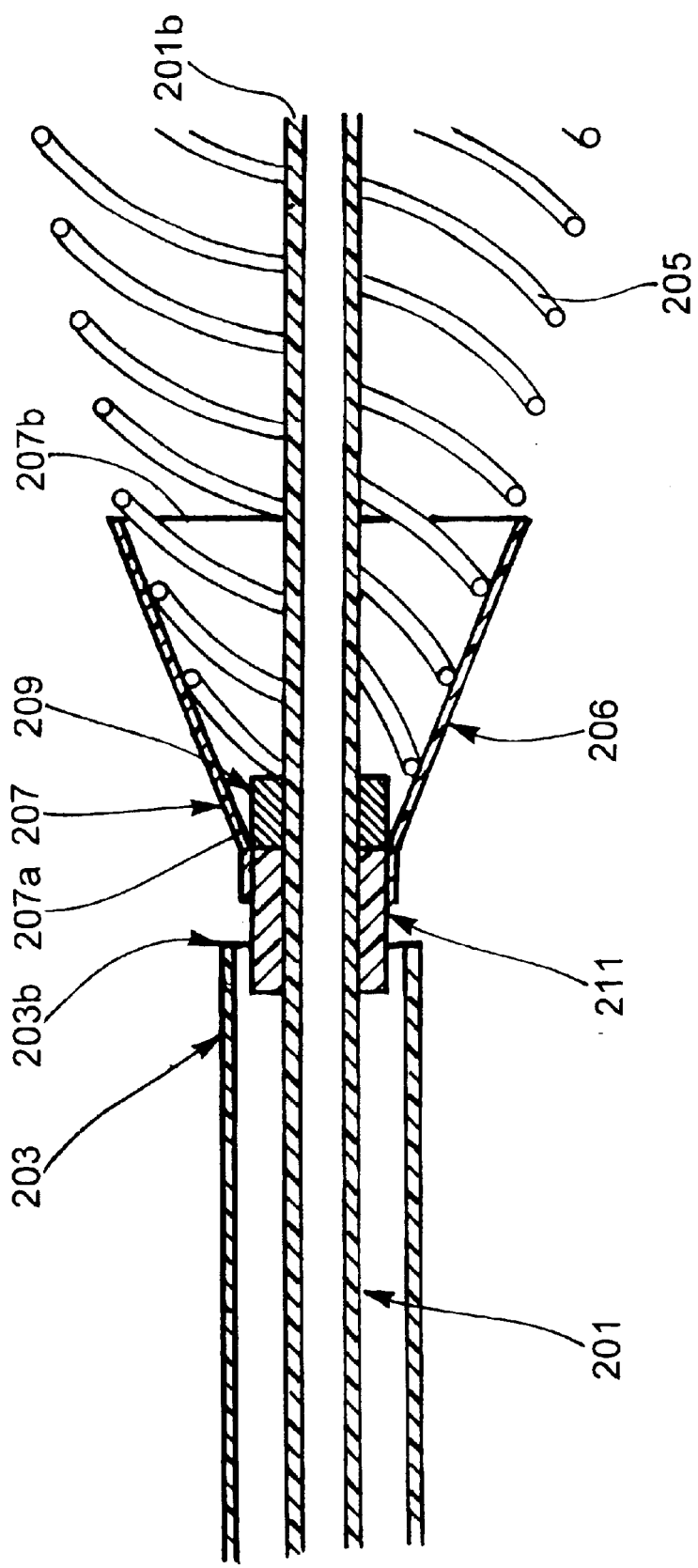
FIG. 5 is a detailed cross sectional view of the distal portion of the stent delivery device of FIG. 4 during the initial stage of inserting a self expanding stent into the stent delivery device.

Capturing element 206, shown in detail in FIG. 5, is provided in order to facilitate easy insertion of the stent into the stent delivery device and protect the proximal extremity of the stent during its insertion in the delivery apparatus by preventing the stent threads from unraveling or bending. Capturing element 206 includes a carriage 211 that may be in the form of a band or ring that surrounds the inner tube 201 and fits within the space between inner tube 201 and outer tube 203 and is slidable longitudinally on the inner tube 201. Attached at the distal end of carriage 211 is a conical or funnel-shaped sleeve 207. The proximal end 207a of the sleeve 207 is fixedly attached to the distal end of carriage 211, such as by adhesive. Sleeve 207 is not rigid, but is foldable such that, when the capturing element 206 is drawn into outer tube 203, sleeve 207 collapses and folds in on itself to fit within outer tube 203. Sleeve 207 may be formed of a thin biocompatible plastic such as polyethylene terepthalate (PET), nylon, polytetraflorethylene (PTFE) or other suitable materials or material combinations. The inside and outside surfaces of the sleeve 207 may have different properties in order to facilitate the grasping of the stent inside the sleeve and the withdrawal of the sleeve into the outer tube of the delivery apparatus. Accordingly, the inner surface of the sleeve may consist of a material or coating having a high coefficient of friction or a rough surface, whereas the outer part of the sleeve may consist of a material having a low coefficient of friction or a slippery coating such as may be achieved with processes like siliconization or hydrogel coating.

In another embodiment, the inside surface of the sleeve may be coated with hydrogel coating that is activated by flushing the device with saline once the stent has been fully loaded in the delivery apparatus, therefore, facilitating the release of the stent from the sleeve at the initiation of stent release.

The distal end 207b of sleeve 207 is open and, in fact, comprises an opening larger than the opening at the distal tip of outer tube 203. The opening at distal end 207b of the sleeve 207 may, but need not, be as large as or larger than the radial diameter of the radially unconstrained stent. In a preferred embodiment, the opening is smaller than the unconstrained diameter of the stent. The opening should be large enough to allow a physician to insert one end of the stent into the sleeve 207 by radially constricting the stent by hand or other implement without too much difficulty. Once an end of the stent is within sleeve 207, it can continue to be pushed into the sleeve 207 (i.e., toward the proximal end of the delivery device) and the inner walls of the sleeve 207 will thereby further radially constrict the end of the stent until the end is constricted to the diameter of the proximal end 207a of the sleeve, which is smaller than the inner diameter of the outer tube 203. At this point, by further pushing the stent proximally and/or drawing the inner tube 201 proximally, the stent will enter the outer tube and be captured within the delivery apparatus in a radially constricted condition between outer tube 203 and inner tube 201.

A separate blocking ring 209 may be fixedly attached to the inner tube 201 distally of the carriage 211. Alternately, separate blocking ring 209 may be formed integrally with the inner tube 201. Separate blocking ring 209 has two primary functions. First, it blocks the end of the stent from being inserted into the delivery device 200 proximally of the blocking ring 209 (and thus proximally of the capturing element 206). It might be possible for the stent to slip into the gap between the inner tube 201 and the carriage 211 of the capturing element 206. Blocking ring 209 prevents this. Further, blocking ring 209 prevents the capturing element from falling off of the end of the inner tube. More particularly, it prevents carriage 211 of the capturing element 206 from moving distally of the blocking ring 209. Particularly, the inner tube 201 will be drawn proximally relative to the outer tube 203 during insertion of stent 205 into the delivery device 200. As the inner tube 201 is drawn proximally, blocking ring 209 will contact carriage 211 of capturing element 206 and draw it proximally along with it. Otherwise, the capturing element 206 would simply fall off of the distal end of the inner tube 201 when the inner tube is drawn proximally into the outer tube 203. Accordingly, blocking ring 209 prevents the capturing element 206 from becoming situated distally of a predetermined point relative to said inner tube.

Figure 6:
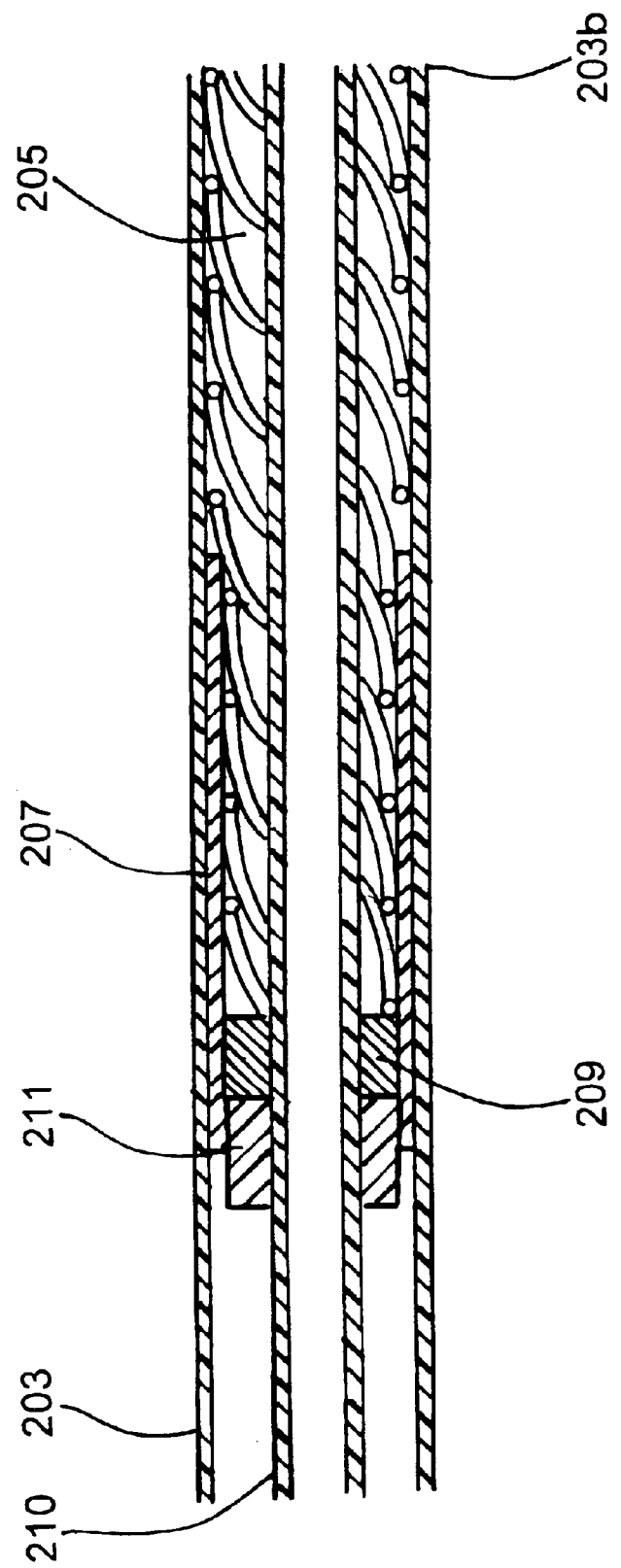
FIG. 6 is a detailed cross sectional view of the distal portion of the stent delivery device of FIG. 4 after the stent has been substantially or completely inserted into the stent delivery device.

Referring now to FIG. 6, when the inner tube 201 and capturing element 206 are drawn proximally relative to the outer tube, foldable sleeve 207 will collapse and fold as it encounters the distal tip 203b of the outer tube and become trapped in a folded state between inner tube 201 and outer tube 203, just as the stent 205 will be captured. FIG. 6 shows the distal end of the delivery device 200 with the stent 205 and capturing element 206 have been inserted into the delivery device 200.

Figure 7:
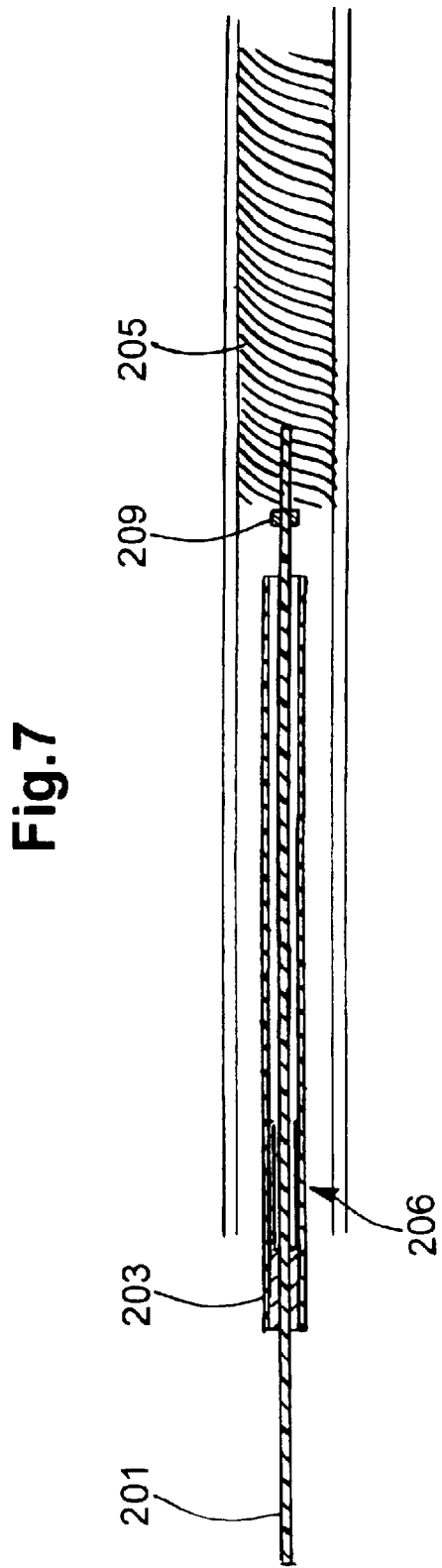
FIG. 7 is a detailed cross sectional view of a stent and stent delivery device after the stent has been released.

The stent and stent delivery device are now ready for a medical procedure in which the stent will be deployed in a body lumen. FIG. 7 illustrates the condition of the stent and stent delivery device after deployment of the stent. When the outer tube 203 is withdrawn while the inner tube 201 remains stationary, the capturing element 206 will likely be drawn along with the outer tube due to frictional engagement of the sleeve 207 with the outer tube 203. Accordingly, sleeve 207 will not protrude from the distal end 203b of the outer tube 203 and therefore not interfere with stent release, as it would if the capturing element was fixed to the inner tube. The blocking ring 209 prevents any proximal motion of the stent relative to the inner tube when the outer tube is withdrawn proximally to release the stent, thereby allowing full stent release when the distal end of the outer tube is withdrawn proximally to the blocking ring.

Figure 8:
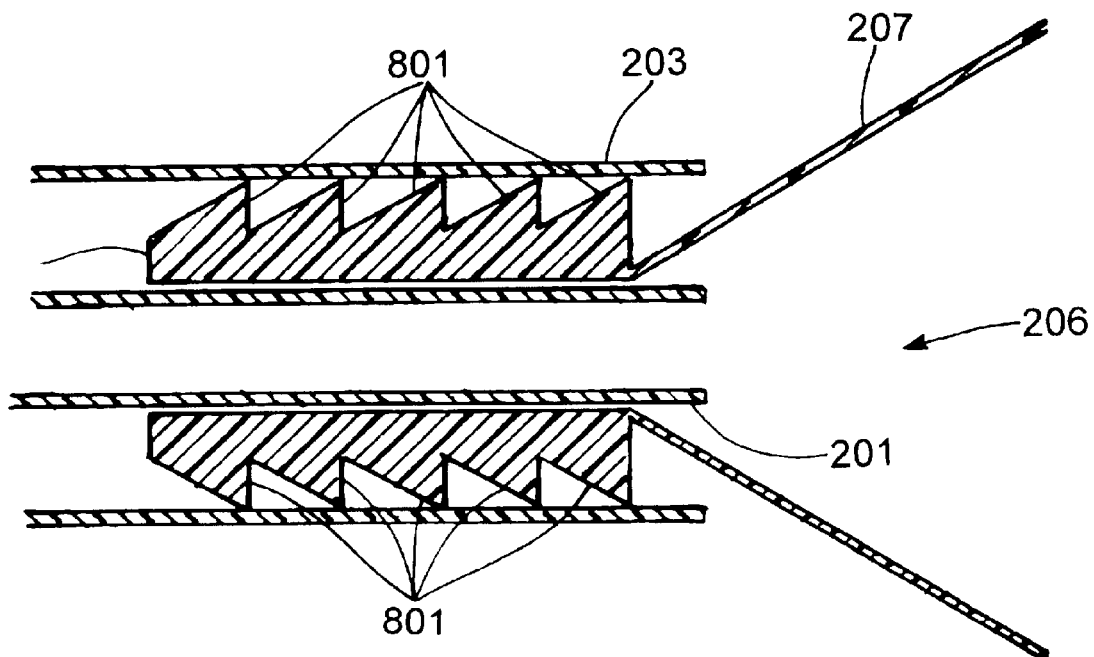
FIG. 8 is a detailed cross sectional view of the capturing element and the distal portion of the delivery device in accordance with one particular embodiment of the invention.
Figure 9:
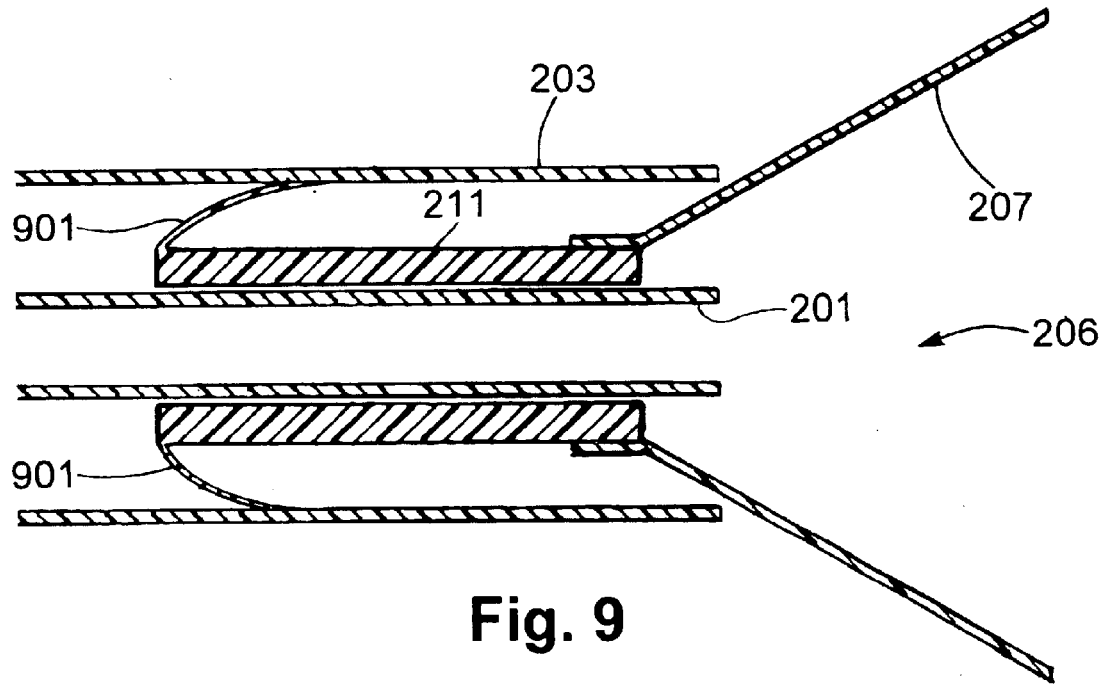
FIG. 9 is a detailed cross sectional view of the capturing element and the distal portion of the stent delivery device in accordance with another particular embodiment of the invention.

FIGS. 8 and 9 illustrate alternative embodiments of the capturing element carriage 211 adapted to help assure the capturing element 206 is drawn along with the outer tube when the outer tube is drawn proximally to release the stent. For instance, FIG. 8 illustrates an embodiment in which carriage 211 includes distally angled barbs 801 that engage the inner surface of the outer tube 203 and resist distal motion of the capturing element 206 relative to the outer tube but allow proximal motion.

FIG. 9 shows an alternative embodiment in which, instead of barbs, one or more leaf springs 901 are positioned on the outer surface of the carriage 211 directed obliquely distally to resist distal motion of the carriage 211 relative to the outer tube 203, but allow proximal motion of the carriage relative to the outer tube.

The sleeve 207 may be made of any suitable polymer, elastomer, or metal. It may be porous, perforated or slotted to allow fluid to flow in the space between said inner tube and said outer tube. In the embodiments shown in the Figures, the inner tube 201 extends beyond the capturing element such that the stent is captured between the inner tube and the outer tube. However, this is not necessary. The blocking element 209 may be attached at the very distal tip of the inner tube 201 such that the stent, when inserted, is captured is within outer tube 203 and there is no inner tube adjacent the stent. The inner tube 201 may be solid or hollow. If hollow, a guide-wire may or may not be used to help guide the delivery apparatus to the stent deployment site.

The components of the capturing element can have material properties that alter in body temperature or in the presence of bodily fluids. For instance, the carriage 211 of the capturing element 206 may be formed of a material that expands when subjected to body temperature or bodily fluids, thus ensuring a sufficiently strong frictional engagement between the inner surface of the outer tube 203 and the carriage 211 to cause it to be carried along with the outer tube 203 when the outer tube is drawn proximally. Further, while the Figures show the carriage 211 and the blocking ring 209 as solid annuluses, this is not necessary. Neither element need be circular nor solid. The same is true of sleeve 207. Longitudinal grooves or holes may be machined in the carriage 211 to allow fluid to flow in the space between the inner tube and the outer tube, for instance, for flushing the catheter prior to use or for the injection of contrast media during the procedure While the invention has hereinabove been described in connection with a standard type of self-expanding stent, it is equally applicable to other forms of stents and, in fact, any tubular self-expanding prosthesis that is delivered in the same general manner. For instance, the invention is equally applicable to stent-grafts and covered stents, both of which are stent-based medical prostheses that are well known to those of skill in the related arts. In fact, it is not even necessary that the prosthesis be self expanding. The invention can be useful in connection with any prosthesis that must be inserted into a small opening.

Having thus described a few particular embodiments of the invention, various alterations, modifications, and improvements will readily occur to those skilled in the art. Such alterations, modifications and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

We claim:

1. An apparatus for delivering a self-expanding stent into a body lumen comprising:
   an outer tube having a proximal end and a distal end and sized to hold a self-expanding stent therein in a radially constricted condition;
   an inner tube within said outer tube having a proximal end and a distal end;
   a capturing element comprising a foldable sleeve slidably engaged with said inner tube, said sleeve having a proximal end and a distal end, said proximal end being smaller than said outer tube and said distal end being larger than said outer tube, said capturing element carried on said inner tube such that said distal end of said sleeve can extend beyond said distal end of said outer tube in an unfolded condition and said sleeve can be drawn into and become folded within said outer tube when said inner tube is drawn proximally relative to said outer tube, whereby a stent having an end inserted into said distal end of said sleeve is drawn into said outer tube, thereby becoming captured in a radially constricted condition within said outer tube; and
   a blocking element fixed to said inner tube near said distal end of said inner tube and adapted to block a stent inserted into said sleeve from becoming situated proximally of said blocking element and to block said capturing element from becoming situated distally of a predetermined point relative to said inner tube.

2. The apparatus of claim 1 wherein said blocking element comprises a band fixed to said inner tube.

3. The apparatus of claim 1 wherein said capturing element further comprises a carriage to which the proximal end of said sleeve is fixedly attached, said carriage at least substantially circumscribing said inner tube so as to be slidable longitudinally on said inner tube.

4. The apparatus of claim 3 wherein said carriage is adapted to engage said outer tube so as to resist distal movement of said capturing element relative to said outer tube to a greater extent than it resists proximal motion of said capturing element relative to said outer tube.

5. The apparatus of claim 4 wherein said carriage comprises a leaf spring extending from said carriage obliquely distally and into engagement with said outer tube, whereby said spring resists distal motion of said carriage relative to said outer tube to a greater extent than it resists proximal motion of said carriage relative to said outer tube.

6. The apparatus of claim 4 wherein said carriage has an outer barbed surface adapted to engage said outer tube and resist distal motion of said carriage relative to said outer tube to a greater extent than it resists proximal motion of said carriage relative to said outer tube.

7. The apparatus of claim 1 wherein said sleeve is funnel shaped.

8. The apparatus of claim 7 wherein said sleeve is conical.

9. The apparatus of claim 1 wherein said distal end of said inner tube extends beyond said blocking element, whereby a stent inserted into said sleeve is captured between said inner tube and said outer tube.

10. The apparatus of claim 1 wherein said sleeve is formed of a thin plastic film.

11. The apparatus of claim 1 wherein said stent is a stent-graft.

12. The apparatus of claim 1 wherein said stent is a covered stent.

13. The apparatus of claim 1 wherein said capturing element includes apertures for allowing fluids introduced between said outer tube and said inner tube to flow between said proximal end of said outer tube and said distal end of said outer tube.

14. A method of loading a stent into a stent delivery apparatus, said apparatus comprising an outer tube sized to hold a self-expanding stent therein in a radially constricted condition, said outer tube having a proximal end and a distal end, an inner tube within said outer tube, said inner tube having a proximal end and a distal end, a capturing element slidably mounted on said inner tube and comprising a foldable sleeve having a proximal end and a distal end, said proximal end being smaller than said outer tube and said distal end being larger than said outer tube, said capturing element carried on said inner tube such that said distal end of said sleeve can extend beyond said distal end of said outer tube in an unfolded condition and said sleeve can be drawn into and become folded within said outer tube when said inner tube is drawn proximally relative to said outer tube and a blocking element fixed to said inner tube near said distal end of said inner tube and adapted to block a stent inserted into said sleeve from becoming situated proximally of said blocking element and to block said capturing element from becoming situated distally of a predetermined point relative to said inner tube, said method comprising the steps of:

(1) positioning said inner tube such that said distal end of said capturing element extends beyond said distal end of said outer tube;

(2) inserting an end of a stent into said distal end of said sleeve; and (3) drawing said inner tube proximally relative to said outer tube so as to draw said sleeve and said stent into said outer tube, thereby capturing said sleeve and said stent in said outer tube in a radially constricted condition.

15. A method of deploying in a body lumen a stent loaded into a stent delivery apparatus in accordance with claim 14 comprising the steps of:

(4) after step (3), inserting said delivery apparatus into a body lumen to position said distal end of said outer tube adjacent a stent deployment site; and (5) after step (4), drawing said outer tube proximally relative to said inner tube and said stent so as to release said stent from its radially constricted condition.

16. The method of claim 14 wherein step (2) comprises inserting said stent into said sleeve until an end of said stent abuts said blocking element.

17. The method of claim 16 wherein, in step (5), said blocking element blocks said stent from being drawn along with said outer tube.

18. The method of claim 17 wherein said blocking element comprises a band fixedly attached to said inner tube distally of said proximal end of said sleeve and wherein, in step (5), said sleeve is drawn along with said outer tube.

19. The method of claim 18 wherein said capturing element further comprises a carriage to which the proximal end of said sleeve is fixedly attached, said carriage circumscribing and frictionally engaging said inner tube so as to be slidable relative to said inner tube upon application of force and wherein an outer surface of said carriage is adapted to engage said outer tube such that said capturing element does not move distally relative to said outer tube when said inner tube is moved distally relative to said outer tube, and wherein, in step (5), said sleeve is drawn along with said outer tube due to said engagement with said outer tube.

20. The method of claim 18 wherein said distal end of said inner tube extends beyond said blocking element, whereby, in step (3), said stent is captured between said inner tube and said sleeve.

* * * * *